United States Patent
Willi et al.

(10) Patent No.: US 7,857,859 B2
(45) Date of Patent: Dec. 28, 2010

(54) FEMUR COMPONENT FOR A HIP JOINT PROSTHESIS

(75) Inventors: Roland Willi, Neftenbach (CH); Aude Leroy Gallissot, Winterthur (CH); Hermann Breimesser, Elgg (CH)

(73) Assignee: Zimmer, GmbH, Winterthur (CH)

( * ) Notice: Subject to any disclaimer, the term of this patent is extended or adjusted under 35 U.S.C. 154(b) by 186 days.

(21) Appl. No.: 12/121,178

(22) Filed: May 15, 2008

(65) Prior Publication Data
US 2008/0228283 A1 Sep. 18, 2008

(30) Foreign Application Priority Data
Jun. 13, 2007 (EP) .................. 07011628
Jul. 17, 2007 (CH) .................. 01180/07

(51) Int. Cl.
*A61F 2/32* (2006.01)
*A61F 2/36* (2006.01)
(52) U.S. Cl. ............... 623/23.35; 623/22.42; 623/23.15
(58) Field of Classification Search ... 623/23.11–23.15, 623/23.35, 20.15, 20.36, 22.42, 22.43, 22.44, 623/22.45, 22.46, 22.4, 19.11, 19.12, 19.13, 623/19.14, 20.35, 22.11
See application file for complete search history.

(56) References Cited

U.S. PATENT DOCUMENTS

| | | | | |
|---|---|---|---|---|
| 4,944,761 A * | 7/1990 | Stuhmer et al. | ......... | 623/23.31 |
| 4,963,155 A * | 10/1990 | Lazzeri et al. | ........... | 623/22.42 |
| 5,002,578 A * | 3/1991 | Luman | .................... | 623/22.42 |
| 5,169,401 A * | 12/1992 | Lester et al. | .................. | 606/79 |
| 5,387,244 A | 2/1995 | Breard | | |
| 5,458,651 A * | 10/1995 | Lawes | ...................... | 623/23.15 |
| 5,507,829 A * | 4/1996 | Thongpreda et al. | ..... | 623/22.41 |
| 5,725,592 A * | 3/1998 | White et al. | ............. | 623/23.35 |
| 5,906,644 A * | 5/1999 | Powell | .................... | 623/20.15 |
| 5,954,771 A * | 9/1999 | Richelsoph et al. | ...... | 623/23.15 |
| 6,179,877 B1 * | 1/2001 | Burke | ...................... | 623/22.12 |
| 6,273,915 B1 * | 8/2001 | Grimes | .................... | 623/23.21 |
| 6,783,553 B2 * | 8/2004 | Grimes | .................... | 623/23.21 |
| 7,044,975 B2 * | 5/2006 | Cheal et al. | .............. | 623/22.42 |
| 7,374,576 B1 * | 5/2008 | Ries et al. | ................. | 623/23.21 |
| 7,534,271 B2 * | 5/2009 | Ries et al. | ................. | 623/23.21 |
| 2004/0107001 A1 * | 6/2004 | Cheal et al. | .............. | 623/22.42 |
| 2007/0043447 A1 * | 2/2007 | Cheal et al. | .............. | 623/22.43 |
| 2007/0219641 A1 * | 9/2007 | Dorr et al. | ............... | 623/22.42 |
| 2007/0255420 A1 * | 11/2007 | Johnson et al. | .......... | 623/22.44 |
| 2008/0133023 A1 * | 6/2008 | Schlotterback et al. | ... | 623/22.42 |

FOREIGN PATENT DOCUMENTS

WO   WO03/034952 A2   5/2003

* cited by examiner

*Primary Examiner*—Alvin J. Stewart
(74) *Attorney, Agent, or Firm*—Baker & Daniels LLP

(57) ABSTRACT

The specified implant for use as a femur component in a hip joint prosthesis comprises a shaft, being intended for the implantation in a cavity of a proximal femur, a head section, for fastening a femoral head prosthesis and a femoral neck section, being arranged between the shaft and the head section. The femoral neck section comprises a femoral head axis and a contour in a cross-section perpendicular to the femoral neck axis, tapering in a V-shape or wedge-shape to medial and at least an anterior straight section and at least a posterior straight section, wherein the straight sections define the tapering.

18 Claims, 3 Drawing Sheets

C-C

D-D

FEMUR COMPONENT FOR A HIP JOINT PROSTHESIS

CROSS REFERENCE TO RELATED APPLICATION

This application claims priority to European Patent Application No. 07 011 628.0 filed on Jun. 13, 2007, and to Swiss Patent Application No. 01180/07 filed on Jul. 17, 2007, the disclosures of which are hereby explicitly incorporated by reference herein.

SUMMARY

The invention relates to an implant for the use as a femur component for a hip joint prosthesis.

The use of hip joint prosthesises can become necessary, when the hip joint of a patient is damaged and thus causes pain and/or is limited in its functionality. In such cases it often becomes necessary, to replace the femoral head and the femoral neck with a prosthesis. The artificial femoral head is fastened to an implant in such a case, wherein the shaft is inserted in the proximal end of the thighbone (femur) that has been prepared accordingly during surgery.

An implant is proposed according to the above mentioned method, wherein besides numerous other advantageous properties, an increased functionality and a higher movement range of the hip joint prosthesis is achieved.

Said implant, for use as a femur component of a joint hip prosthesis, comprises a shaft, being intended for implantation in a cavity of a proximal femur, a head section, being intended for fastening of a femoral head prosthesis, and a femoral neck section, being arranged between the shaft and the head section. The femoral neck section comprises a femoral neck axis and a contour in a cross section perpendicular to the femur neck axis being tapered off in a V- or wedge shape to medial and having at least an anterior straight section and at least a posterior straight section, wherein the linear sections defines the tapering.

In other words, the medially tapered V- or wedge shaped contour configures a medial rib or edge, being anterially or posterially delimited by straight sections. In comparison to a circular or oval contour for example, material in the region of the femoral neck of the implant is saved and the femoral section is designed in a slimmer way, wherein the movement range of the femur component in relation to a respective hip-side component of the hip joint prosthesis, particularly in the anatomically relevant areas, is increased. At the same time, sufficient high stability of the implant is guaranteed.

In one embodiment of the implant, the contour comprises, at least along a part of the femoral neck section, each a lateral and a medial straight section anterially and posterially, encompassing an angle being different from zero.

In a further embodiment of the implant, the femoral neck section comprises an anterior and posterior flattening, being formed of a lateral straight section of the contour in a cross section perpendicular to the femoral neck axis. Said flattening provides an increased optimization of the femoral neck section in regard to the stability properties of the implant and the movability of the hip joint prosthesis.

In a further embodiment of the implant, the contour varies from proximal to distal, which is to say, the configuration of the contour changes depending to the position of an observed cross section perpendicular to the femoral neck axis in respect to the longitudinal extension of the femoral neck section.

In a further embodiment of the implant, the contour is allocated in a circle, the center thereof being on the femoral neck axis.

In a further embodiment of the implant, the diameter of the circle increases from proximal to distal.

In a further embodiment of the implant, the contour comprises a lateral circular segment and a medial circular segment, having the same radius of curvature and the same center of curvature. In other words, the lateral and the medial circular segments are circular arcs, both being sections of a common circle.

In a further embodiment of the implant, the femoral neck axis lies in the femoral neck plane and the medial circular segment lies in the femoral neck plane, particularly on the femoral neck axis.

In a further embodiment of the implant, the radius of curvature increases from proximal to distal.

In a further embodiment of the implant, the length of the lateral circular segment decreases from proximal to distal.

In a further embodiment of the implant, the length of the medial circular segment, at least in a middle part of the femoral neck section is basically constant.

The different indicated embodiments of an implant according to the independent claim for the implant and the implemented characteristics can of course be combined amongst themselves.

In the following, the invention will be further described with illustrated examples of the embodiment in the drawings. The examples of the embodiment and the drawings are only intended to be instructive and not for the limitation of the objects described in the claims. The illustrations in the drawings are simplified; details not necessary for the comprehension of the invention are omitted.

BRIEF DESCRIPTION OF THE DRAWINGS

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

Figure 1A:
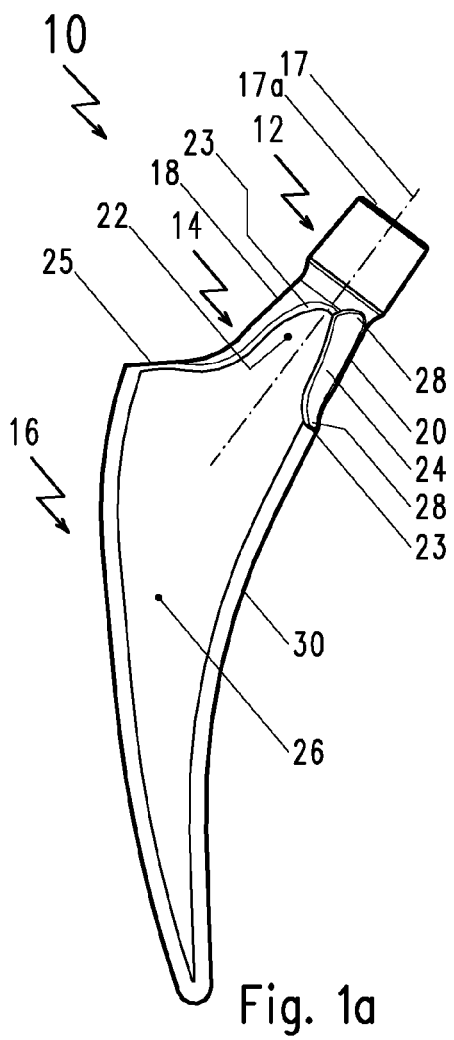
FIG. 1*a* shows a perspective image of an embodiment of the implant in an anterior view.

The embodiment of an implant 10 shown in FIG. 1*a* to 1*d* for the use as femur component of a hip joint prosthesis, comprises a head section 12, a femoral neck section 14 and a shaft 16. The head section 12 serves for the fastening of a femoral head prosthesis not shown, and merges distally into the femoral neck section 14. The distal end of the femoral neck section 14 is connected to the shaft 16. The shaft 16 is intended for the implantation in a cavity of a proximal femur (not shown). The longitudinal extension of the femoral neck section 14 is defined by the femoral neck axis 17, extending concentrically through the head section 12 perpendicular to a distal front face 17a of the head section 12.

The femoral neck section 14 comprises a lateral boundary surface 18 and a medial boundary surface 20. Between the lateral boundary surface 18 and the medial boundary surface 20, an anterior-lateral boundary surface 22 and an anterior-medial boundary surface 24 extend, being inclined relative to each other. It should be mentioned in this context, that "anterior" is only used for the simplification of terms, as it is easily noticeable, that particularly the anterior-medial boundary surface 24 is arranged so as to be inclined to a front plane and to a sagital plane of the implant 10. A respective posterior-lateral boundary surface 22a and a respective posterior-medial boundary surface 24a cannot be seen in FIG. 1a. The boundary surfaces 22a, 24a can be referred to in FIG. 1b to 1d.

In other words, the medially arranged boundary surfaces 20, 24, 24a configure an, regarding stability and functionality, optimized medial rib or a wedge- or V-shaped edge, being tapered towards medial. The anterior-lateral boundary surface 22 and the posterior-lateral boundary surface 22a configure flattenings, thus material not being of considerable importance for the stability of the implant 10 can be saved and the range of mobility of the hip joint prosthesis can thus be increased.

The anterior-lateral boundary surface 22 increases in its extent from proximal to distal along the femoral neck axis 17 in width—which is to say, in the medial-lateral extent perpendicular to the femoral neck axis 17—while the anterior-medial boundary surface 24 initially increases in width and then decreases to distal again. The lateral boundary surface 18 exhibits a complimentary path to the anterior-lateral boundary surface 22 and decreases in its extent from proximal to distal in width—which is to say, in anterior-posterior extension perpendicular to the femoral neck axis 17.

It merges into an implant shoulder 25 of the shaft 16. The medial boundary surface 20, starting at the head section 12, first is narrower and then widens at a middle part with essentially constant width.

Figure 1B:
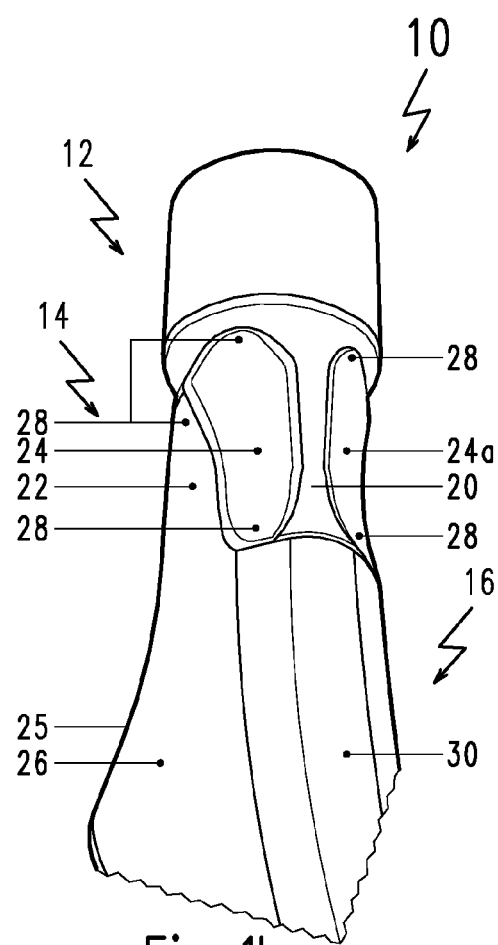
FIG. 1*b* to 1*d* respectively show a perspective image of the proximal region of the implant of FIG. 1*a* from different angles.

FIG. 1b shows, in comparison to FIG. 1a, the proximal part of the implant 10 from a distally and medially shifted angle, wherein the design of the femoral neck section 14 is more clearly recognizable.

Obviously, the anterior-lateral boundary surface 22 merges basically steadily into an anterior shaft surface 26, wherein the anterior-medial boundary surface 24 ends proximally. Between the medial boundary surface 20 and a medial shaft surface 30 is a convex curvature, as the distal section of the medial boundary surface 20 and the proximal section of the medial shaft surface 30 are each curved concavely, wherein the curvature radius is however different.

In the proximal section of the anterior-lateral boundary surface 22, a concave curved section 28 is present, wherein the medial boundary surfaces 20, 24, 24a also comprise two concave curved sections 28.

The transitions between the boundary surfaces 18, 20, 22, 22a, 24, 24a and/or the shaft surfaces 25, 26, 30 are rounded off by rounding elements 23.

Figure 1C:
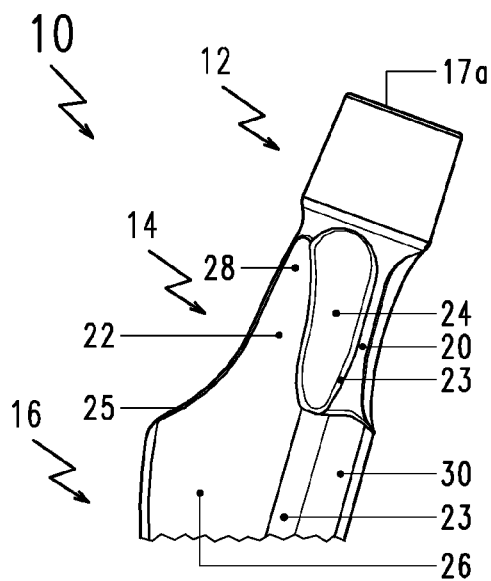
Figure 1D:
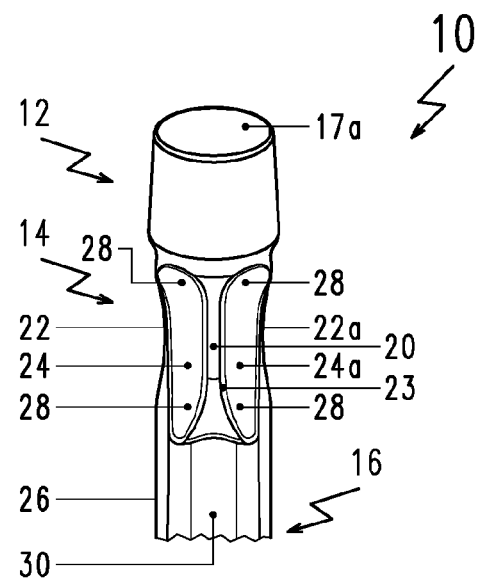

FIGS. 1c and 1d show further views of the proximal part of the implant 10 for clarification of the above-mentioned aspects in particular.

Simplified, the femoral neck section 14 is formed at least in the middle section by a truncated cone, being tapered towards the head section 12. The basic form deviates in a proximal part and a distal part of the femoral neck section 14 from a truncated cone.

The truncated cone is trimmed by partially curved surfaces, as explained in the following. By trimming of the truncated cone, the femoral neck section 14 takes up less room than in conventional implants, making the femur component of the hip joint prosthesis in relation to the components facing the hip more moveable. The volume of the femoral neck section 14 is thus reduced by configuring a medial rib and by including anterior and posterior flattenings, as to imitate the anatomical functionality and the range of motion of a natural hip joint in a superior way.

Figure 2A:
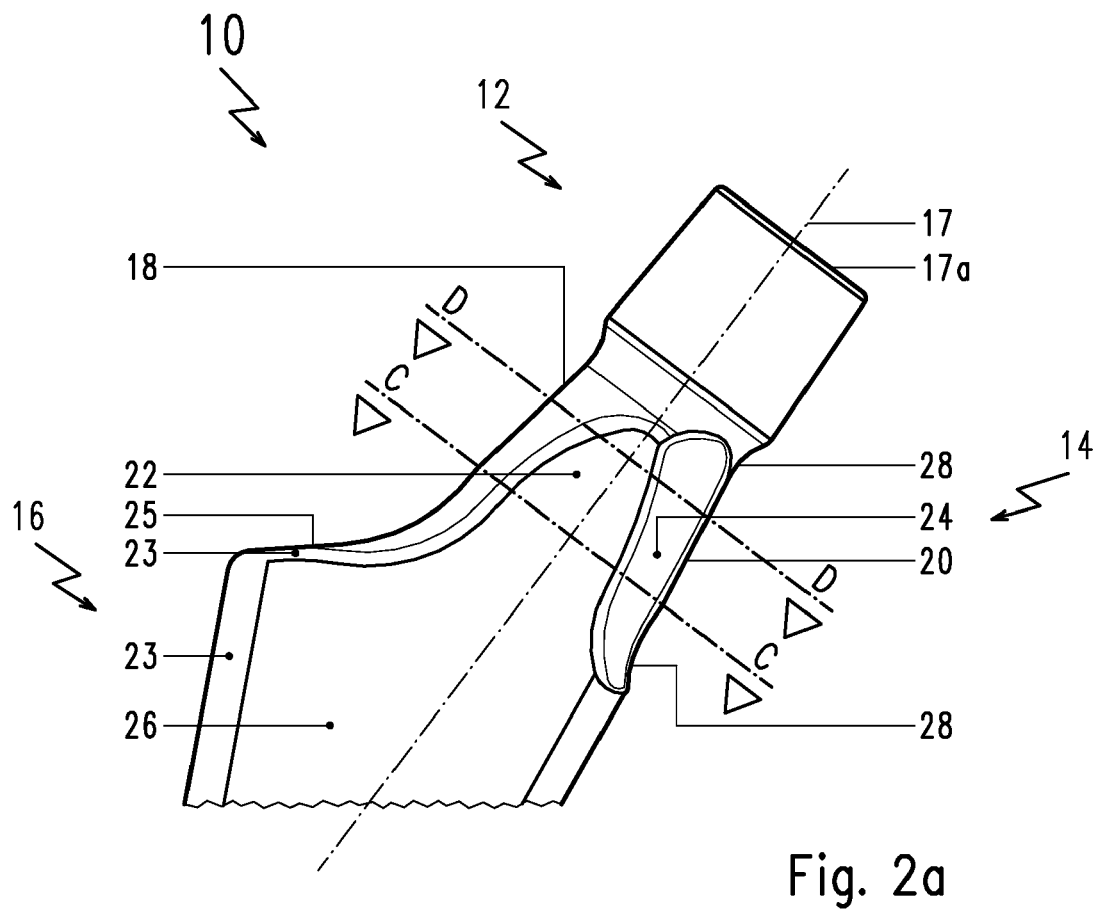
FIGS. 2*a* and 2*b* schematically each show the proximal region of an embodiment of the implant from an anterior or an anterior-medial view.
Figure 2B:
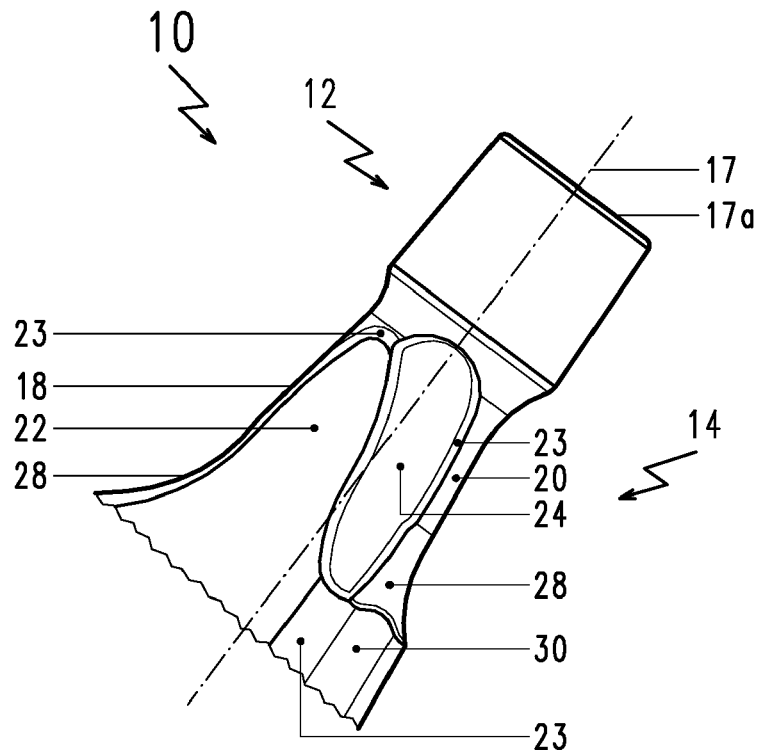

FIGS. 2a and 2b show schematic figures of the proximal part of the implant 10, to illustrate the physical arrangement and configuration of the different boundary surfaces 18, 20, 22, 24 and shaft surfaces 26, 30 in particular. In FIG. 2a the position of a proximal sectional plane D-D and a distal sectional plane C-C is marked, both extending perpendicular to the femoral neck axis 17, wherein the proximal sectional plane D-D is arranged closer to the head section 12 than the distal sectional plane C-C.

Figure 3A:
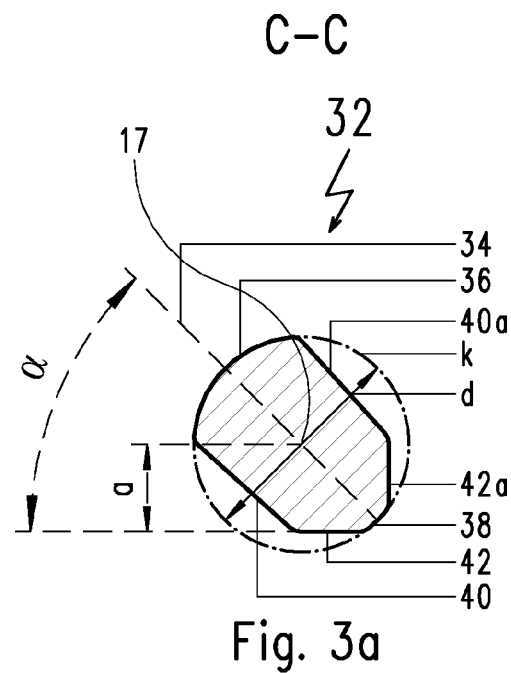
FIGS. 3*a* and 3*b* schematically each show a cross section of the femoral neck section of the embodiment of the implant of FIG. 2*a*.
Figure 3B:
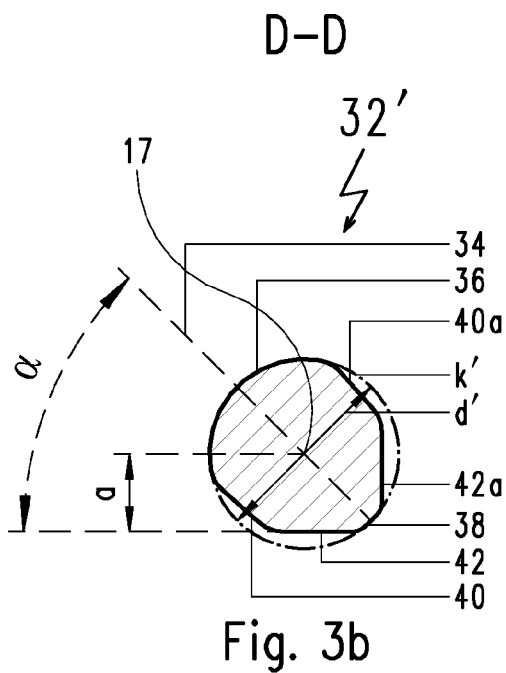

FIGS. 3a and 3b show a contour 32 and 32' of the cross-section of the femoral neck section 14 in the sectional planes C-C and D-D.

Contour 32 of FIG. 3 exhibits a primarily symmetrical run in relation to the femoral neck section 34. Contour 32 comprises a lateral circular segment 36 and a medial circular segment 38 as well as an anterior-lateral straight segment 40, an anterior-medial straight segment 42, a posterior-lateral straight segment 40a and a posterior-medial straight segment 42a, forming in the run of the femoral neck section 14 the lateral boundary surface 18 and the medial boundary surface 20, as well as the anterior-lateral boundary surface 22, the anterior-medial boundary surface 24, the posterior-lateral boundary surface 22a and the posterior-medial boundary surface 24a.

The circular segments 36, 38 are segments of a circle K, the center thereof lying on the femoral neck axis 17 which is running in the femoral neck plane 34. The circular segments 36, 38 exhibit the same curvature radius and a common curvature center. The circle K has a diameter d. It is obvious, that the contour 32 is allocated in the circle K. In other words, the contour 32 is obtained by originating from the circle K with four steps along the straight sections 40, 42, 40a, 42a.

The anterior-medial straight section 42 and the femoral neck plane 34 contain an angle α, being for example at 45°, the contour 32 tapering to medial. Also the anterior-lateral straight section 40 is not perpendicular to the femoral neck plane 34, wherein the tapering by the anterior-lateral straight section 40 is considerably smaller than the respective tapering caused by the run of the anterior-medial straight section 42. Due to the already mentioned symmetry of the contour 32 the same applies to the posterior straight sections 40a, 42a.

The contour 32' of FIG. 3b describes the cross-section of the femoral head section 14 in the sectional plane D-D being arranged closer to the head section 12 than the sectional plane C-C. As the femoral head section 14 varies along the femoral head axis 17 in the cross-section form, as depicted in FIG. 1a to 1d and 2a and 2b, the form of contour 32' differs from the form of contour 32.

Thus, the diameter d' of the circle K' surrounding contour 32'—the center being arranged on the femoral neck axis 17—is smaller than the diameter d of contour 32. Furthermore, the anterior lateral straight section 40 and posterior lateral straight section 40a are offset perpendicular to the outside compared to the arrangement in contour 32, so that the incline of the anterior lateral straight section 40 and posterior lateral straight section 40*a* stays the same in relation to the femoral neck plane 34. The anterior lateral straight section 40 and posterior lateral straight section 40*a* are now shorter than the medial straight sections 42, 42*a*, although the angle α' of contour 32' is the same as angle α of contour 32. Furthermore, the length of the lateral circular segment 36 of contour 32' is longer than the respective length of contour 32. In addition, the distance a', due to the smaller diameter d', changes between the center of the circle and the anterior-medial straight section 42. The distance a' is thus smaller than a respective distance a of the contour 32.

The cited parameters are also influenced by the curved sections 28 of the boundary surfaces 18, 20, 22, 22*a*, 24, 24*a*, although being arranged proximally and distally to the sectional plane D-D and C-C.

Due to the increase of the circular diameter d, d' to proximal, the above indicated truncated cone is defined by being "shortened" by the straight sections 40, 40*a*, 42, 42*a*. The "shortening" is achieved by slanted planes, creating a two-stage tapering in the cross-section of the femoral neck section 14 on the one hand, and on the other hand are also slanted in a proximal-distal direction and/or have curvatures, as already explained with FIG. 1*a* to 2*b*.

By combining different slant angles and/or inclines and/or curvatures, numerous configurations of the femoral neck section can be realized, wherein the cross-section contours may also deviate from the described symmetrically arranged cross-section contours. For example, the provision of a hourglass basic body instead of the truncated cone is also possible.

Figure 3C:
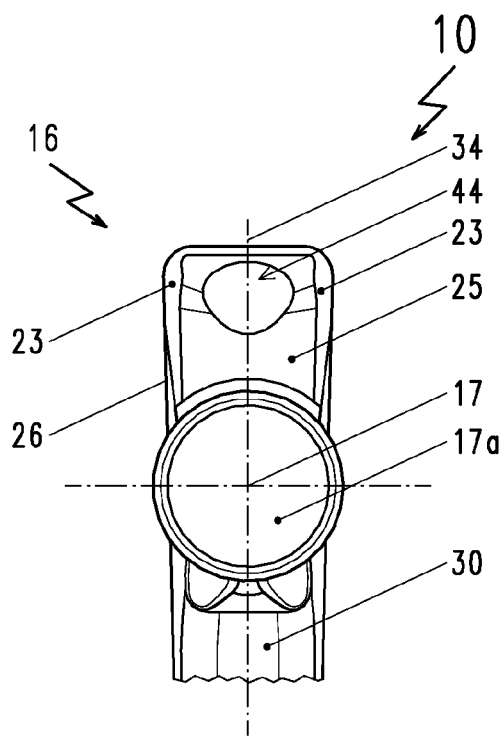
FIG. 3*c* schematically shows an embodiment of the implant from a proximal view.

FIG. 3*c* shows a view of an embodiment of the implant 10 perpendicular to the distal face side 17*a* of the head section 12. The implant shoulder 25 is depicted, comprising a bore 44 for fastening an impact adapter (not shown) on the shaft 16 of the implant 10. The impact adapter is used for impacting the implant 10 into the femur, to avoid direct hits on the implant 10. Furthermore, FIG. 3 shows, the femoral neck plane 34 coming together with a symmetrical plane of the shaft 16, at least of the proximal section.

Figure 3D:
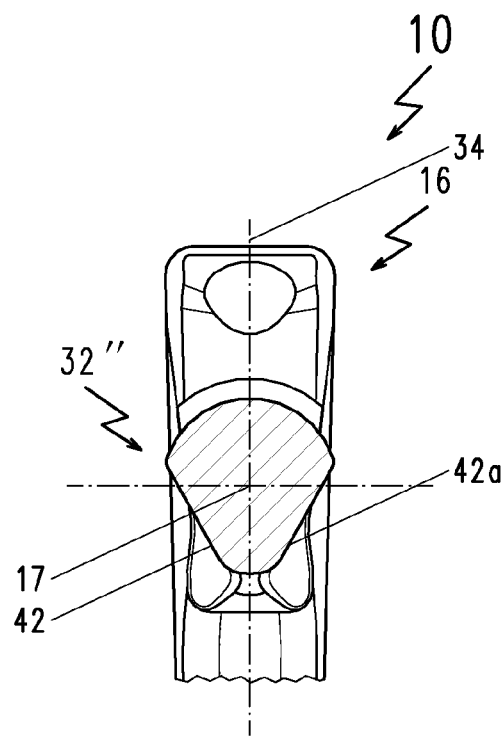
FIG. 3*d* shows a further embodiment of the implant from proximal, wherein the head section was omitted, to be able to show the contour of the femoral neck section.

FIG. 3*d* shows an embodiment of the implant 10, wherein no anterior-lateral boundary surface 22 and no posterior-lateral boundary surface 22*a* is provided. This embodiment does not contain the above-mentioned anterior and posterior flattenings and is thus essentially defined by a medial rib, having a distinctive wedge- or V-form. The anterior and the posterior section of the contour 32" of the shown femoral neck cross-section are configured by the medial straight sections 42 and 42*a*.

In the light of the embodiments presented herein, further embodiments regarding the invention characterized in the claims open up for a person of ordinary skill in the relevant art. They cannot be presented here conclusively.

All chosen indications about alignments, positions, orientations and directions, particularly concerning anatomical axis, planes, directions in the room and directions of movement in the claims and the description and the drawings, are known to the specialist and refer to the implanted state of the implant.

The invention claimed is:

1. An implant for use as a femur component of a hip joint prosthesis, comprising:
   a shaft being intended for the implant in a cavity of a femur;
   a head section intended for the fastening of a femoral head prosthesis; and
   a femoral neck section having a proximal section and a distal section, said femoral neck section being arranged between the shaft and the head section wherein the femoral neck section comprises a femoral head axis and a contour in a cross-section perpendicular to the femoral head axis, the contour comprising a lateral circle segment and a medial circle segment having the same curvature radius and a common curvature center, the contour tapering in one of a V-shape or a wedge-shape towards said medial circle segment and comprising an anterior segment and a posterior segment wherein the anterior and posterior segments define the tapering, the curvature radius increases along said femoral neck section from said proximal section to said distal section.

2. The implant according to claim 1, wherein the contour comprises, at least along a part of the femoral neck section, an anterior medial section and a posterior medial section.

3. The implant according to claim 2, wherein the contour comprises an anterior lateral straight section and a posterior lateral straight section, wherein the femoral neck section comprises an anterior and posterior flattening, said anterior flattening being configured in a cross-section perpendicular to the femoral neck axis from said anterior lateral straight section of the contour, said posterior flattening being configured in a cross-section perpendicular to the femoral neck axis from said posterior lateral straight section of the contour.

4. The implant in accordance with claim 1, wherein the contour varies along said femoral neck section from said proximal section to said distal section.

5. The implant in accordance with claim 1, wherein the contour is enclosed by a circle, the center thereof being on the femoral neck axis.

6. The implant according to claim 5, wherein the diameter of the circle increases along said femoral neck section from said proximal section to said distal section.

7. The implant according to claim 1, wherein the femoral neck axis is located in a femoral neck plane and the curvature center lies in the femoral neck plane on the femoral neck axis.

8. The implant according to claims 1, wherein the length of the medial circle segment is substantially constant along the femoral neck section in at least a middle part of the femoral neck section.

9. The implant according to claim 1, wherein the anterior segment and the posterior segment comprise straight segments.

10. An implant for use as a femur component of a hip joint prosthesis, comprising:
    a shaft being intended for the implant in a cavity of a femur;
    a head section intended for the fastening of a femoral head prosthesis; and
    a femoral neck section having a proximal section and a distal section, said femoral neck section being arranged between the shaft and the head section wherein the femoral neck section comprises a femoral head axis and a contour in a cross-section perpendicular to the femoral head axis, the contour comprising a lateral circle segment and a medial circle segment having the same curvature radius and a common curvature center, the contour tapering in one of a V-shape or a wedge-shape towards said medial circle segment and comprising an anterior segment and a posterior segment wherein the anterior and posterior segments define the tapering, the length of the lateral circle segment decreases from said proximal section to said distal section.

11. The implant according to claim 10, wherein the contour comprises, at least along a part of the femoral neck section, an anterior medial section and a posterior medial section.

12. The implant according to claim 11, wherein the contour comprises an anterior lateral straight section and a posterior lateral straight section, wherein the femoral neck section comprises an anterior and posterior flattening, said anterior flattening being configured in a cross-section perpendicular to the femoral neck axis from said anterior lateral straight section of the contour, said posterior flattening being configured in a cross-section perpendicular to the femoral neck axis from said posterior lateral straight section of the contour.

13. The implant in accordance with claim 10, wherein the contour varies along said femoral neck section from said proximal section to said distal section.

14. The implant in accordance with claim 10, wherein the contour is enclosed by a circle, the center thereof being on the femoral neck axis.

15. The implant according to claim 14, wherein the diameter of the circle increases along said femoral neck section from said proximal section to said distal section.

16. The implant according to claim 10, wherein the femoral neck axis is located in a femoral neck plane and the curvature center lies in the femoral neck plane on the femoral neck axis.

17. The implant according to claims 10, wherein the length of the medial circle segment is substantially constant along the femoral neck section in at least a middle part of the femoral neck section.

18. The implant according to claim 10, wherein the anterior segment and the posterior segment comprise straight segments.

* * * * *